US009961895B2

(12) United States Patent
Hughes et al.

(10) Patent No.: US 9,961,895 B2
(45) Date of Patent: *May 8, 2018

(54) ADDITIVES FOR USE IN WOOD PRESERVATION

(71) Applicant: ARCH TIMBER PROTECTION LIMITED, Castleford, West Yorkshire (GB)

(72) Inventors: Kevin Hughes, Pontefract (GB); Craig Mars, Eggborough (GB); Andrew Hughes, Pontefract (GB)

(73) Assignee: ARCH TIMBER PROTECTION LIMITED, Castleford, West Yorkshire (GB)

(*) Notice: Subject to any disclaimer, the term of this patent is extended or adjusted under 35 U.S.C. 154(b) by 0 days. days.

This patent is subject to a terminal disclaimer.

(21) Appl. No.: 15/600,439

(22) Filed: May 19, 2017

(65) Prior Publication Data

US 2017/0251661 A1   Sep. 7, 2017

Related U.S. Application Data

(63) Continuation of application No. 15/185,624, filed on Jun. 17, 2016, which is a continuation of application No. 14/268,736, filed on May 2, 2014, now Pat. No. 9,603,358, which is a continuation-in-part of application No. PCT/GB2012/000826, filed on Nov. 1, 2012.

(30) Foreign Application Priority Data

Nov. 4, 2011  (GB) .................................. 1119139.2

(51) Int. Cl.
| | |
|---|---|
| C09D 5/16 | (2006.01) |
| A01N 25/22 | (2006.01) |
| A01N 59/16 | (2006.01) |
| A01N 59/20 | (2006.01) |
| B27K 3/22 | (2006.01) |
| A01N 43/00 | (2006.01) |
| A01N 55/02 | (2006.01) |

(52) U.S. Cl.
CPC ............. *A01N 25/22* (2013.01); *A01N 43/00* (2013.01); *A01N 55/02* (2013.01); *A01N 59/16* (2013.01); *A01N 59/20* (2013.01); *B27K 3/22* (2013.01); *B27K 2240/20* (2013.01); *Y10T 428/662* (2015.04)

(58) Field of Classification Search
None
See application file for complete search history.

(56) References Cited

U.S. PATENT DOCUMENTS

| | | |
|---|---|---|
| 4,567,272 A | 1/1986 | Orth et al. |
| 4,632,991 A | 12/1986 | Maurer et al. |
| 4,801,404 A | 1/1989 | Dietrich et al. |
| 4,839,373 A | 6/1989 | Ito et al. |
| 4,929,454 A | 5/1990 | Findlay et al. |
| 4,950,685 A | 8/1990 | Ward |
| 4,970,201 A | 11/1990 | Giebeler et al. |
| 5,186,947 A | 2/1993 | Goettsche et al. |
| 5,248,450 A | 9/1993 | Metzner et al. |
| 5,304,237 A | 4/1994 | Barth et al. |
| 5,385,926 A | 1/1995 | Ludwig et al. |
| 5,407,920 A | 4/1995 | Dawson |
| 5,714,507 A | 2/1998 | Valcke et al. |
| 5,804,591 A | 9/1998 | Valcke et al. |
| 5,874,025 A | 2/1999 | Heuer et al. |
| 5,916,356 A | 6/1999 | Williams et al. |
| 5,972,971 A | 10/1999 | Heuer et al. |
| 5,977,168 A | 11/1999 | Konishi et al. |
| 5,990,043 A | 11/1999 | Kugler et al. |
| 6,211,218 B1 | 4/2001 | Goettsche et al. |
| 6,242,440 B1 | 6/2001 | De Witte et al. |
| 6,248,761 B1 | 6/2001 | Fujimoto |
| 6,323,224 B1 | 11/2001 | Tsuboi et al. |
| 6,506,795 B1 | 1/2003 | Barth et al. |
| 6,521,288 B2 | 2/2003 | Laks et al. |
| 6,558,685 B1 | 5/2003 | Kober et al. |
| 6,936,624 B2 | 8/2005 | Tsuboi et al. |
| 7,307,070 B2 | 12/2007 | Heuer et al. |
| 7,323,187 B1 | 1/2008 | Schur |
| 7,632,567 B1 | 12/2009 | Zhang et al. |
| 7,674,481 B2 | 3/2010 | Leach et al. |

(Continued)

FOREIGN PATENT DOCUMENTS

| | | |
|---|---|---|
| AU | 2007203237 A1 | 2/2008 |
| CA | 2238033 A1 | 5/1997 |

(Continued)

OTHER PUBLICATIONS

Schubert, et al: "Protection of Wood from microorganisms by laccase-catalysed iodination", Applied and Environmental Microbiology, American Society for Microbiology, US, vol. 78, No. 20, Oct. 1, 2012 (Oct. 1, 2012), pp. 7267-7275.

Ursula Kues, "Wood Production, Wood Technology and Biotechnological Impacts", 2007, Universitatsverlag Gottingen, Available online at http://webdoc.sub.gwdg.de/univerlag/2007/wood_production.pdf.

International Search Report and Written Opinion for International Application No. PCT/US2015/028616 dated Aug. 3, 2015. (11 pages).

(Continued)

*Primary Examiner* — Robert T Butcher
(74) *Attorney, Agent, or Firm* — Lucas & Mercanti, LLP

(57) ABSTRACT

The present invention relates to a wood preservative formulation comprising a biocidal agent which is a copper or zinc ion complexed with an amino compound selected from the group consisting of ammonia, a water soluble amine or alkanolamine and an aminocarboxylic acid and a stabilizer, as well as to aqueous treatment solutions comprising such a formulation and methods of treating wood or other cellulosic material utilising said formulation.

27 Claims, 3 Drawing Sheets

(56) References Cited

U.S. PATENT DOCUMENTS

| | | |
|---|---|---|
| 2001/0000184 A1 | 4/2001 | Konishi et al. |
| 2001/0051649 A1 | 12/2001 | Heuer et al. |
| 2002/0083864 A1 | 7/2002 | Higaki |
| 2003/0010956 A1 | 1/2003 | Las et al. |
| 2004/0016909 A1 | 1/2004 | Zhang et al. |
| 2004/0211721 A1 | 10/2004 | Stamets |
| 2004/0258768 A1 | 12/2004 | Richardson et al. |
| 2004/0258838 A1 | 12/2004 | Richardson et al. |
| 2005/0080089 A1 | 4/2005 | Tiedink et al. |
| 2005/0227956 A1 | 10/2005 | Wang et al. |
| 2006/0112850 A1 | 6/2006 | Zhang et al. |
| 2006/0251915 A1 | 11/2006 | Jin et al. |
| 2006/0252847 A1 | 11/2006 | Hayward et al. |
| 2006/0257578 A1 | 11/2006 | Zhang et al. |
| 2006/0269583 A1 | 11/2006 | Garst et al. |
| 2006/0276468 A1 | 12/2006 | Blow |
| 2007/0021385 A1 | 1/2007 | Zhang et al. |
| 2007/0032584 A1 | 2/2007 | Lochel et al. |
| 2007/0082187 A1 | 4/2007 | Wang et al. |
| 2007/0142410 A1 | 6/2007 | Garnier |
| 2007/0151476 A1 | 7/2007 | Humar et al. |
| 2008/0046277 A1 | 2/2008 | Stamets |
| 2008/0108680 A1 | 5/2008 | Bruns et al. |
| 2008/0132569 A1 | 6/2008 | Chang et al. |
| 2008/0138371 A1 | 6/2008 | Amrhein et al. |
| 2008/0187669 A1 | 8/2008 | Kingma et al. |
| 2008/0193640 A1 | 8/2008 | Zhang et al. |
| 2009/0158961 A1 | 6/2009 | Zhang et al. |
| 2009/0203643 A1 | 8/2009 | Patel |
| 2009/0280185 A1 | 11/2009 | Richardson et al. |
| 2010/0068545 A1 | 3/2010 | Zhang et al. |
| 2011/0030579 A1 | 2/2011 | Koop et al. |
| 2013/0209823 A1 | 8/2013 | Mars et al. |

FOREIGN PATENT DOCUMENTS

| | | |
|---|---|---|
| CN | 1633853 A | 7/2005 |
| CN | 1319456 C | 6/2007 |
| EP | 0554833 A1 | 8/1993 |
| EP | 2036435 A1 | 3/2009 |
| JP | 2003252705 A | 9/2003 |
| WO | 9302557 A1 | 2/1993 |
| WO | 9702119 A1 | 1/1997 |
| WO | 9718713 A1 | 5/1997 |
| WO | 0128331 A1 | 4/2001 |
| WO | 2004091875 A2 | 10/2004 |
| WO | 2006118980 A2 | 11/2006 |
| WO | 2007053252 A1 | 5/2007 |
| WO | 2009014106 A1 | 1/2009 |
| WO | 2011038747 A1 | 4/2011 |
| WO | 2011161404 A1 | 12/2011 |
| WO | 2013064798 A1 | 5/2013 |

OTHER PUBLICATIONS

Australian Patent Examination Report No. 3 for Australian Patent Application No. 2011268757 dated Aug. 27, 2013 (3 pages).
Search Report under Section 17 for GB1110545.9 dated Oct. 21, 2011. (3 Pages).
International Search Report and Written Opinion for International Application No. PCT/GB2011/000930 dated Sep. 16, 2011. (10 Pages).
Ullmann's Encyclopedia of Industrial Chemistry, 6th edition, vol. 39, 2003, pp. 489.
Freeman et al., "A comprehensive Review of Copper-Based Wood Preservatives with a focus on new micronized or dispersed copper-systems", Forest Products Journal, vol. 58, No. 11, pp. 6-27.
Schmidt, Wood and Tree Fungi, Biology, Damage, Protection, and Use, Springer, 2006, pp. 152.
Groot et al., "Using copper-tolerant fungi to biodegrade wood treated with copper based preservatives", International Biodeterioration & Biodegradable, 1999, vol. 44, pp. 17-27.
European Patent Office Communication of a notice of opposition issued in connection with a related EP Application No. 11729649.1 (published as EP 2582234), which was dated Oct. 27, 2015 and concerns papers submitted by an opponent, Koppers Performance Chemicals (24 pages).
European Patent Office Communication of a notice of opposition issued in connection with a related EP Application No. 11729649.1 (published as EP 2582234), which was dated Oct. 29, 2015 and concerns papers submitted by an opponent, Frank Marek (18 pages).
English translation of JP 2003-252705A, cited as item No. 10 under Foreign Patent Documents (9 pages).
English translation of CN 1319456 C, cited as item No. 18 under Foreign Patent Documents (7 pages).
Printout from Wikipedia, "Antrodia", http://en.wikipedia.org/wiki/Antrodia, printed Oct. 20, 2015 (4 pages).
Printout from Wikipedia, "Fomitopsis Palustris", https://en.wikipedia.org/wiki/Fomitopsis_palustris, printed Oct. 20, 2015 (1 page).
Machine English translation of WO 2009/014106 A1, cited as item No. 16 under Foreign Patent Documents (8 pages).
Nikiforova et al., "Copper Ion Sorption by Cellulose Sorbents Modified with Hydrophilic Nitrogen-Containing Polymers", ISSN 1070-4272, Russian Journal of Applied Chemistry, 2010, vol. 83, No. 7, pp. 1170-1175.
European Patent Office Communication of a notice of opposition issued in connection with a related EP Application No. 11729649.1 (published as EP 2582234), which was dated Oct. 27, 2015 and concerns papers submitted by an opponent, BASF Wolman GmbH, and its English translation (19 pages).

ADDITIVES FOR USE IN WOOD PRESERVATION

CROSS-REFERENCE TO RELATED APPLICATIONS

This application is a Continuation of U.S. patent application Ser. No. 15/185,624, filed Jun. 17, 2016, which is a Continuation of U.S. application Ser. No. 14/268,736, filed May 2, 2014, which in turn is a Continuation-in-Part of PCT International Application No. PCT/GB2012/000826, filed Nov. 1, 2012, which claims benefit of British Application No. 1119139.2, filed Nov. 4, 2011, the contents of each of which are incorporated herein by reference.

FIELD OF THE INVENTION

The present invention relates to wood preservative formulations and methods of treating wood and other cellulosic material. In particular it relates to formulations which contain a positively charged polymer which enhances the penetration of the active ingredients also present in the formulation into the wood or other cellulosic material.

BACKGROUND OF THE INVENTION

Many types of wood preservative treatments exist on the market today. These can be applied directly to the surface, paint-on, or by vacuum pressure immersion treatments. During industrial application of preservatives, timber is typically impregnated with the treatment solution to achieve either shell or full cell type penetration into the substrate.

Depending on the wood species being treated and the end use, the depth of penetration of the preservative solution into the timber can have a significant bearing on the useful service life of the treated timber.

A typical industrial treatment plant will consist of a storage tank to hold the treatment solution and an autoclave. Timber is charged into the autoclave and this is then flooded with treatment solution. Combinations of vacuum and pressure are applied to achieve the required penetration of preservative into the timber.

During the treatment process, an amount of preservative solution is consumed by way of being absorbed into the timber. This typically represents a relatively small amount of the total volume of solution used to flood the autoclave. This generates a scenario whereby treatment solution is repeatedly exposed to timber. The average treatment solution age increases as a function of solution refresh rates. This can extend from several days to many months. Therefore the solution is repeatedly exposed to timber.

SUMMARY OF THE INVENTION

It has been observed that the ability of the preservative to penetrate into the timber substrate as the solution is repeatedly exposed to timber can deteriorate very significantly. This can have significant consequences to the useful service life of the treated article.

Wood preservatives tend to be neutral or alkaline and the high pHs can solubilise chemical substances found in timber and during the impregnation process the timber generates anionic by-products. This combination of anionic by-products and timber extractives can then hinder penetration of the wood preservatives through the timber.

It has been found that addition of certain highly cationic polymers to the wood preservative solutions can significantly improve preservative solution uptakes and penetration into the wood being treated.

Thus, in a first aspect, the present invention provides a wood preservative formulation comprising a biocidal agent and a stabilizer. The stabilizer is a cationic polymer, an enzyme, an organic polymer, a quaternary ammonium compound and/or a mixture thereof. The stabilizer is present in an amount effective to stabilize the wood preservative composition which allows the wood preservative component to effectively penetrate a wood substrate intended to be protected by the wood preservative composition.

DETAILED DESCRIPTION OF THE INVENTION

Figure 1:
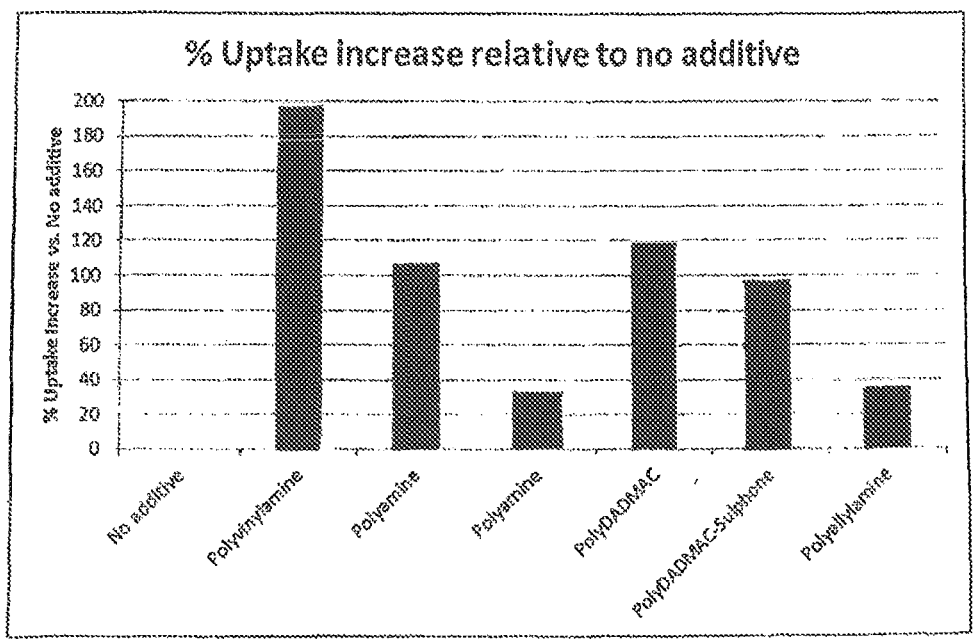
FIG. 1 is a graph showing % gains in solution uptake achieved during impregnation of a copper MEA solution into *Pinus sylvestris* with various cationic polymer additives of the invention.

The stabilizer polymer used in the preservative composition includes chitosan; cationic derivative of natural polymers such as guar gum, starch, cellulose and hydroxycellulose; a polymer or copolymer having one or more of the following repeating units of formula (I), (II), (III) or (IV):

(i) a repeating unit of formula (I)

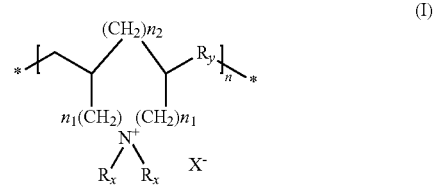

(ii) a repeating unit of formula (II)

(iii) a repeating unit of formula (III)

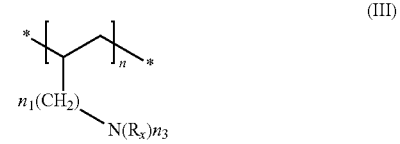

(iv) a repeating unit of formula (IV)

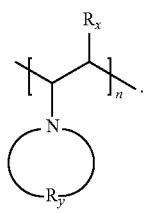

in which:
n=3 to 5000;
$n_1$=0, 1 or 2;
$n_2$=0 or 1;
$n_3$=2 or 3 and when n=3 the nitrogen atom carries a positive charge and a counter ion $X^-$ is present;
$R_x$ groups, which can be identical or different, are hydrogen or a straight chain, branched or cyclic alkyl, alkenyl, alkynyl, alkanoxyl, aryl,
—(C=O)H, —(C=O)$R_n$, —$CO_2$H —$CO_2R_n$, —$CH_2CO_2$H, —$CH_2CO_2R_n$, $CH_2NR_nR_n$,
—(C=O)$NR_nR_n$, —CN, —$(CH_2)n_4$—O—$R_n$, in which;
$R_n$ groups, which can be identical or different, are hydrogen or a straight chain, branched or cyclic alkyl, alkenyl, alkynyl, alkanoxyl or aryl;
$n_4$=2 or 3;
$R_y$ is a divalent group having one or more of the following groups $V_1$-$V_8$

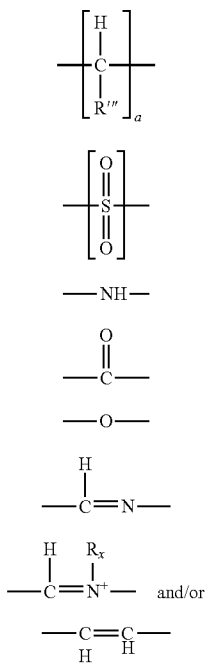

in which;
$R_z$ is H, OH, or $N(R)_x$;
a is 0 to 20; and
$X^-$ is any anion selected from chloride, bromide, iodide, fluoride, sulphate, phosphate, carboxylate especially propionate and lactate, carbonate, bicarbonate, nitrate, nitrite, hydroxide, cyanide;

$R_x$ groups are preferably $C_{1-22}$, more preferably $C_{1-16}$, e.g. $C_{1-8}$ alkyl, alkenyl, alkynyl or alkanoxyl, or $C_{5-22}$, more preferably $C_{6-10}$ aryl.

Likewise $R_n$ groups are preferably $C_{1-22}$, more preferably $C_{1-16}$, e.g. $C_{1-8}$ alkyl, alkenyl, alkynyl or alkanoxyl, or $C_{5-22}$, more preferably $C_{6-10}$ aryl. Aryl groups may be heteroaromatic.

The molecular weight of the above polymers is typically up to 1,000,000, preferably up to 500,000, preferably at least 1,000, more preferably between 1,000 and 50,000.

As discussed in more detail below, many wood preservatives contain biocidal metal compounds, such as copper compounds, in which the metal ion acts as the primary fungicide. It is known in the art to use nitrogen containing compounds, such as monoethanolamine, as a complexing agent for the metal ion to enhance delivery of the metal into the wood. In such systems the complexing nitrogen compound is typically present at between 5 and 25% by weight of ingredients in the concentrated wood preservative formulation which is manufactured. In contrast, according to the present invention, where the cationic polymers are not included for the purposes of complexing a copper or other metal ion but to manage negatively charged extractives and by-products, the wood preservative formulation preferably contains 0.01 to 4%, more likely 0.05 to 2% by weight of a cationic polymer as defined above, more preferably 0.1 to 1%, most preferably 0.15 to 0.6%. These values refer to the amount of cationic polymer present in the wood preservative concentrate as manufactured and supplied to the treatment site. Such formulations are typically diluted with water to form treatment solutions which are 2-6% solutions on a m/v basis. The amount of cationic polymer applied to the wood will thus be correspondingly less in terms of the weight percentage of the impregnation solution.

The wood preservative formulations of the invention may comprise as a biocidal agent, inter alia, one or more of the following active agents; biocidal metal compounds (in which the metal ion is the active biocidal agent); boron containing biocides such as boric acid, oxides and salts thereof and organic fungicides including fungicidal amides such as prochloraz, penthiopyrad, dichlofluanid and tolylfluanid; anilide fungicides such as sedaxane and penflufen; anilinopyrimidine fungicides such as pyrimethanil, cyprodinil or mepanipyrim; fungicidal aromatic compounds such as chlorthalonil, cresol, dicloran, pentachlorophenol, sodium pentachlorophenol, 2-(thiocyanatomethylthio)-1,3-benzothiazole (TCMBC), dichlorophen, fludioxonil and 8-hydroxyquinoline; fungicidal heterocyclic compounds such as dazomet, fenpropimorph, bethoxazin and dehydroacetic acid; strobilurins such as azoxystrobin; quaternary ammonium compounds; azoles; isothiazolones; Potassium HDO (cyclohexylhydroxydiazene 1-oxide, potassium salt); pyrion compounds such as sodium pyrithione, zinc pyrithione, copper pyrithione, 1-hydroxy-2-pyridinone and pyrion disulfide and mixtures thereof. Particularly preferred organic fungicidal agents are quaternary ammonium compounds, azoles, and mixtures thereof.

Preferred quaternary ammonium compounds are trimethyl alkyl quaternary ammonium compounds such as cocotrimethyl ammonium chloride; dialkyldimethyl quaternary ammonium compounds such as didecyl dimethyl ammonium chloride, didecyl dimethyl ammonium carbonate, didecyl dimethyl ammonium bicarbonate, dioctyl dimethyl ammonium chloride and octyl decyl dimethyl ammonium chloride, or mixtures thereof; alkyl dimethyl or diethyl benzyl ammonium salts such as benzalkonium chloride and benzalkonium hydroxide; polyethoxylated quaternary ammonium compounds such as N,N-didecyl-N-methyl-poly (oxyethyl) ammonium propionate (Bardap 26) or N,N-didecyl-N-methyl-poly(oxyethyl) ammonium lactate; and N-substituted pyridinium compounds such as cetyl pyridinium chloride.

Particularly preferred quaternary ammonium compounds are benzalkonium chloride, didecyl dimethyl ammonium chloride and didecyl dimethyl ammonium carbonate, with didecyl dimethyl ammonium chloride and didecyl dimethyl ammonium carbonate being the most preferred. It is noted that the quaternary ammonium compound may further enhance the penetration of the biocidal agent into the wood or cellulosic substrate.

The azole compound, i.e. a compound comprising an azole group, may be an imidazole or a 1,2,4-triazole and is preferably represented by the general formula (V)

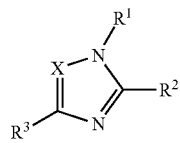

(V)

wherein
X denotes $CR^4$ or N;
$R^1$ denotes hydrogen or a linear, branched, cyclic, aromatic or any combination thereof, saturated or unsaturated, substituted or unsubstituted $C_1$ to $C_{40}$ group
wherein any of the carbon atoms other than those bound to the nitrogen atom shown in formula (V) may be replaced with an optionally substituted hetero atom;
$R^2$ denotes hydrogen, $C_1$-$C_8$ alkyl, $C_2$-$C_8$ alkenyl, $C_6$-$C_{10}$ aromatic, $C_5$-$C_{10}$ heteroaromatic or $C_1$-$C_4$ alkyl carbamate; and
$R^3$ and $R^4$ denote hydrogen; or
together $R^3$ and $R^4$ may provide a benzimidazole group (i.e. $R^3$ and $R^4$ may combine to form —$(CH)_4$—).

The formulations of the invention may contain one or more azole compounds, such as mixtures of an imidazole and a 1,2,4-triazole, or mixtures of two or more 1,2,4-triazoles. However, it is preferred to use 1,2,4-triazoles in the formulations of the invention.

The imidazole compound incorporates a five-membered diunsaturated ring composed of three carbon atoms and two nitrogen atoms at non-adjacent positions. The imidazole compound may be a benzimidazole. Preferred compounds include thiabendazole, imazalil, carbendazim and prochloraz.

The 1,2,4-triazole compound incorporates a five-membered diunsaturated ring composed of three nitrogen atoms and two carbon atoms at non-adjacent positions.

Preferred triazole compounds include a triazole compound selected from compounds of formula (VI):

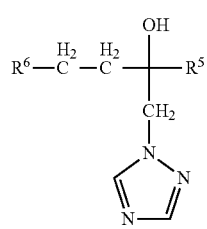

(VI)

wherein $R^5$ represents a branched or straight chain $C_{1-5}$ alkyl group (e.g. t-butyl) and $R^6$ represents a phenyl group optionally substituted by one or more substituents selected from halogen (e.g. chlorine, fluorine or bromine) atoms or $C_{1-3}$ alkyl (e.g. methyl), $C_{1-3}$ alkoxy (e.g. methoxy), phenyl or nitro groups.

Alternatively, the triazole compound is advantageously selected from compounds of formula (VII):

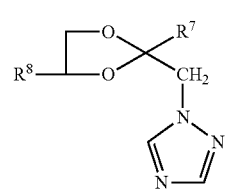

(VII)

wherein $R^7$ is as defined for $R^6$ above and $R^8$ represents a hydrogen atom or a branched or straight chain $C_{1-5}$ alkyl group (e.g. n-propyl).

Particularly preferred triazoles include, but are not limited to, triadimefon, triadimenol, triazbutil, propiconazole, cyproconazole, difenoconazole, fluquinconazole, tebuconazole, flusilazole, uniconazole, diniconazole, bitertanol, hexaconazole, azaconazole, flutriafol, epoxyconazole, tetraconazole, penconazole, ipconazole, prothioconazole and mixtures thereof.

Particularly preferably the wood preservative formulation comprises a biocidal metal ion, in preferred embodiments, the biocidal metal ion is a biocidal copper ion. The biocidal copper may advantageously be incorporated into the formulation in the form of inorganic copper salts, such as carbonate, bicarbonate, sulphate, nitrate, chloride, hydroxide, borate, fluoride or oxide. Alternatively, the copper may be in the form of a simple organic salt, such as formate or acetate, or as a complex such as N-nitroso-N-cyclohexyl-hydroxylamine-copper (copper-HDO) or copper pyrithione (bis(2-pyridylthio)copper 1,1'-dioxide, CAS number 14915-37-8).

Preferably, the biocidal copper ion is a copper (II) ion. Preferred forms of copper (II) include basic copper carbonate ($CuCO_3 \cdot Cu(OH)_2$), copper (II) acetate, copper (II) hydroxide, copper (II) oxide and copper (II) sulphate pentahydrate, with basic copper carbonate being the most preferred. Preferred copper (I) compounds that can be used are copper (I) oxide and copper-HDO.

Particularly preferred biocidal copper compounds are selected from basic copper carbonate, copper (II) acetate, copper (II) sulphate pentahydrate, copper (II) hydroxide, copper (II) oxide, copper (I) oxide, and copper-HDO.

In alternative preferred embodiments, the biocidal metal ion may be a biocidal zinc ion. The biocidal zinc may advantageously be incorporated into the formulation in the form of inorganic zinc salts, such as carbonate, bicarbonate, chloride, hydroxide, borate, oxide or phosphate. Alternatively, the zinc may be in the form of a an organozinc compound such as a simple organic salt, such as formate or acetate, or as a complex such as N-nitroso-N-cyclohexyl-hydroxylamine-zinc (zinc-HDO), zinc naphthenate or zinc pyrithione (bis(2-pyridylthio)zinc 1,1'-dioxide—CAS number 13463-41-7).

Preferred zinc compounds include zinc oxide, zinc carbonate, zinc chloride, zinc borate and zinc pyrithione, with zinc oxide, zinc carbonate and zinc borate being the most preferred.

The metal may be included in the formulation of the invention as a solubilised metal ion. Suitable methods for solubilising metal ions such as copper and zinc are known in the art, for example from WO93/02557. Suitable complexing agents for the copper or zinc include, for example, polyphosphoric acids such as tripolyphosphoric acid; ammonia; water soluble amines and alkanolamines capable of complexing with copper or zinc cations; aminocarboxylic acids such as glycine, glutamic acid, ethylenediaminetetraacetic acid (EDTA), hydroxyethyldiamine triacetic acid, nitrilotriacetic acid and N-dihydroxy ethylglycine. Where the complexing agents are acidic in nature they may be employed either as free acids or as their alkali metal or ammonium salts. These complexing agents may be used either alone or in combination with each other. Preferred complexing agents are selected from alkanolamines, such as monoethanolamine, diethanolamine, triethanolamine, monopropanolamine, dipropanolamine, and tripropanolamine. Ethanolamines are preferred, with monoethanolamine being particularly preferred.

Preferred formulations of the invention comprise a biocidal agent which is a copper or zinc ion complexed with an amino compound selected from the group consisting of ammonia, a water soluble amine or alkanolamine and an aminocarboxylic acid. Preferred amino compounds are discussed herein and particularly preferred amino compounds are ammonia, monoethanolamine and primary, secondary or tertiary amines incorporating a $C_{8-14}$ alkyl, preferably $C_{12}$ alkyl, e.g. laurylamine or dimethyl laurylamine.

Alternatively viewed, preferred formulations contain a zinc or copper compound and an amino compound selected from the group consisting of ammonia, a water soluble amine or alkanolamine and an aminocarboxylic acid. The amino compound complexes with the metal ion to solubilise it.

In some embodiments, particularly where the formulation contains zinc, it may be advantageous to have two solubilising and/or complexing agents, for example an amino compound as discussed above and a gluconate salt such as sodium gluconate.

Preferred wood preservative systems for use with the stabilizers defined above are known as alkaline copper quaternary systems, comprising a copper compound and a quaternary ammonium compound, for example as defined above. Further preferred wood preservative formulations contain an azole as defined above and a biocidal metal ion as defined above. More preferred formulations contain a copper compound and a triazole, preferably together with an alkanolamine. Particularly preferred formulations contain copper carbonate present as an ethanolamine complex and tebuconazole, e.g. as sold under the Tanalith® brands.

Exemplary cationic polymers for use in the formulations of the invention include: chitosan, cationic derivatives of natural polymers including guar gum, starch, cellulose and hydroxyl cellulose; Polydiallyldimethylammonium chlorides (polyDADMAC), including polyDADMAC-co-sulphones (DADMAC-co-SO2), polyDADMAC-co-hydroxyethylcellulose (DADMAC-co-HEC), polyDADMAC-co-acrylamide (DADMAC-co-AM), polyDADMAC-co-acrylic acid (DADMAC-co-AA), and acrylic acid-DADMAC-acrylamide terpolymers (AA-co-DADMAC-AM); Polydiallylmethylamine chlorides (polyDAMAmC), including epichlorohydrin derivatives; Polydiallyamine chlorides (polyDAAmC), including polyDAAmC-co-sulphones (DAAmC-co-SO2), polyDAAmC-co-maleic acid (DAAmC-co-MA); polyallylamines (polyAAm) including polyDAAmC-co-AAm; polyamines, including branched and linear epihalohydrin derivatives of polyamines or polyamidoamines, branched and linear polyethyleneimines (PEI), and polyionenes; polyvinyl amines (PVAm) including vinyl amine/vinyl formamide copolymers, polyvinyl imidazole, and quaternized polyvinyl imidazole; polyamides; polyvinyl amides, including polyvinyl pyrrolidone and polyvinyl caprolactam; polyvinyl formamides; poly(acryloyloxy trimethyl ammonium (polyAcETA) or poly(methacryloyloxyethyl trimethyl ammonium) (polyMacETA) salts including polyMacETA-co-acrylamide (MacETA-co-Am), and polyMacETA-co-vinyl pyrrolidone (MacETA-co-VP); poly(acrylamidopropyl trimethyl ammonium) (polyAmPTA) or poly(methacrylamidopropyl trimethyl ammonium) (polyMamPTA) salts, including polyMamPTA-co-vinyl pyrrolidone (MamPTA-co-VP) and poly(acrylic acid-co-MamPTA-co-methyl acrylate) (AA-co-MamPTA-co-Mac). Exemplary cationic natural polymers include, for example, Guar Hydroxypropyltrimonium Chloride (Guar gum 2-hydroxy-3-(trimethylammonio) propyl ether chloride CAS#65497-29-2); Hydroxypropyl Guar Hydroxypropyltrimonium Chloride (Guar gum, 2-hydroxypropyl 2-hydroxy-3-(trimethylammonio)propyl ether, chloride CAS#71329-50-5); Starch Hydroxypropyltrimonium chloride (Starch, 2-hydroxy-3-(trimethylammonio)propyl ether, chloride CAS#56780-58-6); Cellulose, omega-ether with alpha-2-hydroxy-3-(trimethylammonio) propyl-omega-hydroxypoly (oxy-1,2-ethanediyl) chloride (Polyquaternium-10, CAS#68610-92-4); Hydroxyethyl cellulose dimethyl diallylammonium chloride copolymer (Polyquaternium-4 CAS#92183-41-0); and chitosan (CAS#9012-76-4).

Exemplary polyionenes include, for example, Poly[(dimethyliminio)-1,3-propanediyl(dimethyliminio)-1,6-hexanediylbromide (1:2)] (Hexadimethrine Bromide, Ionene-6,3 Bromide; CAS#28728-55-4), Poly [(dimethyliminio)-1,3-propanediyl(dimethyliminio)-1,6-hexanediylchloride (1:2)] (Hexadimethrine Chloride, Ionene-6,3 Chloride; CAS#68393-49-7), Poly[oxyethylene (dimethyliminio) ethylene (dimethylimino) ethylene dichloride] (Polixetonium chloride, Polyquaternium 42; CAS#31512-74-0), Poly[(dimethyliminio)-1,3-propanediylbromide(1:1)] (Ionene-3,3; CAS#31622-87-4), Poly[(dimethyliminio)-1,6-hexanediylbromide (1:1)] (Ionene-6,6; CAS#31622-88-5), Poly[(dimethyliminio)-1,6-hexanediyl (dimethyliminio)-1,10-decanediyldibromide(1:2)] (Ionene-6,10; CAS#28728-57-6), Poly[(dimethyliminio)-1,2-ethanediyl(dimethyliminio)-1,5-pentanediylbromide(1:2)] (Ionene-2,5; CAS#51325-19-0), [α-[4-[Tris(2-hydroxyethyl)ammonio]-2-buten-1-yl]-ω-[tris(2-hydroxyethyl)ammonio]poly[(dimethyliminio)-2-butene-1,4-diyl Chloride] Chloride; (Polidronium Chloride; Polyquaternium 1; CAS#75345-27-6), and Poly[bis(2-chloroethyl)ether 1,3-bis [3-(dimethylamino)propyl]urea] quaternized (Polyquaternium 2; CAS#68555-36-2).

Preferred cationic polymers for use in the formulations of the invention include:
Poly vinyl formamides,
Poly amides,
Poly vinyl amides,
Polyamines, branched and linear, specifically polyamines derived from epihalohydrin,
Poly vinyl amines (PVAm),
PolyDADMAC's,
Poly allyl amines (PAAm),
Polyionenes,
PolyDADMAC Sulphones, and
Vinyl amine/vinyl formamide copolymers.

Particularly preferred are polyvinylamines, poly DADMAC and poly DADMAC-sulphone and polyamines (both high and low MW polyamines). Most preferred is a polyamine, in particular a polyamine with a molecular weight of about 1,000 to 10,000, for example 2,000 to 4,000.

Generally the cationic polymer will have a molecular weight of about 1,000 to about 10,000, and typically will be in the range of about 2,000 to about 5,000. The preservative composition will generally contain between about 0.001% to about 10% by weight of the cationic polymer; typically between about 0.01% to about 4.0% by weight. A particularly useful range of the cationic polymer is in the 0.01 and 1.0%.

Other stabilizers may be used either in place of or in combination with the cationic polymer and/or the quaternary ammonium compound. Such stabilizers include enzymes, organic polymers and mixtures thereof, wherein the stabilizer is present in an amount which will allow the preservative composition to effectively penetrate the wood being protected.

Particular enzymes include for example a lipase, lipoxygenase, esterase, laccase, peroxidase, pectinase, protease, amylase, cellulase, and/or xylanase.

Particular organic polymers include for example an acrylamide polymer or copolymers, and/or polyethylene oxide or copolymer.

Particular quaternary ammonium compounds include trimethylalkyl quaternary ammonium compounds such as cocotrimethyl ammonium chloride; dialkyldimethyl quaternary ammonium compounds such as didecyl dimethyl ammonium chloride, didecyl dimethyl ammonium carbonate, didecyl dimethyl ammonium bicarbonate, dioctyl dimethyl ammonium chloride and octyl decyl dimethyl ammonium chloride, or mixtures thereof; alkyl dimethyl or diethyl benzyl ammonium salts such as benzalkonium chloride and benzalkonium hydroxide; polyethoxylated quaternary ammonium compounds such as N,N-didecyl-N-methyl-poly(oxyethyl) ammonium propionate (Bardap 26) or N.N-didecyl-N-methyl-poly(oxyethyl) ammonium lactate; and N-substituted pyridinium compounds such as cetyl pyridinium chloride.

Of these quaternary ammonium compounds of particular interest are benzalkonium chloride, didecyl dimethyl ammonium chloride and didecyl dimethyl ammonium carbonate. Of these quaternary ammonium compounds, didecyl dimethyl ammonium carbonate has been found to be particularly effective.

In some instances it is preferable to prepare the wood preservative formulation from two or more products shortly before administration, thus in a further aspect, the present invention provides a combined wood preservative product comprising, (a) a biocidal agent as defined herein; and
(b) a stabilizer polymer as defined herein.

The product will typically contain a first compartment or container containing a formulation comprising (a) and a second compartment or container containing the polymer (b). The product may be supplied with written instructions for mixing and diluting (in any order) the two parts.

The formulation or product is typically diluted prior to application to the timber as an impregnation or treatment solution, the biocidal agent containing part may be diluted first before addition of the polymer. Dilution is preferably with water, e.g. at a ratio of water:concentrate v/v of 10:1 to 200:1, preferably 20:1 to 100:1, more preferably 20:1 to 50:1.

The treatment solution will preferably contain 10 or 50 to 1000 ppm of cationic polymer, more preferably 50 or 100 to 500 ppm (ppm=parts per million by weight).

In a further aspect, the invention provides a method of preserving wood or other cellulosic material which comprises applying to the wood or other cellulosic material a formulation of the invention as described above or applying the individual components to the wood/material such that the wood/material effectively receives a formulation as described.

Reference to "individual components" is not to be understood as requiring separate application of each active ingredient but as indicating that the whole complement of active and other ingredients are not simultaneously applied. Thus, the material is treated in such a way which means that it effectively receives a wood preservative formulation of the invention.

Types of wood which can benefit from treatment with the formulations of the invention include sawn timber, logs, glulam, plywood, laminated veneer lumber (LVL), wood based composite products such as oriented strand board (OSB), medium density fibreboard (MDF), fibreboard, hardboard and particle board.

It will be understood that "wood" in the context of this invention does not encompass living trees or other plants.

Other cellulosic materials which can benefit from treatment with the formulations of the invention are lignocellulosic substrates, wood plastic composites, cardboard and cardboard faced building products such as plasterboard, and cellulosic material such as cotton. Also, leather, textile materials and even synthetic fibres, hessian, rope and cordage as well as composite wood materials. For convenience, the invention is described with reference to the treatment of wood but it will be appreciated that other cellulosic materials may be treated analogously. The reference to treatment of "wood" or "timber" applies mutatis mutandis to such substrates, unless it is clear from the context. Preferably, though not exclusively, the formulations are applied to sawn timber, logs or laminated veneer lumber, OSB or MDF. Most preferably, the formulations are applied to unseasoned timber.

Conveniently, the formulations of the present invention are applied as a liquid composition. They may also be applied as a solid implant or paste. Preferably, the formulations are applied as a liquid composition, e.g. in the form of an emulsion made up of solubilised liquid droplets. Preferably, the emulsions are in the form of a microemulsion. The person skilled in the art of making emulsions knows how to make an emulsion according to the invention by the use of suitable solvents and emulsifying agents.

Preferably, when applied in liquid form, this is in an aqueous solution, but one or more organic solvents or a mixture of water and an organic solvent could also be used. Suitable organic solvents include both aromatic and aliphatic hydrocarbon solvents such as white spirit, petroleum distillate, kerosene, diesel oils and naphthas. Also, glycol ethers, benzyl alcohol, 2-phenoxy ethanol, methyl carbitol, propylene carbonate, benzyl benzoate, ethyl lactate and 2-ethyl hexyl lactate.

The application of these formulations may be by one or more of dipping, deluging, spraying, brushing or other surface coating means or by impregnation methods, e.g. high pressure or double vacuum impregnation into the body of the wood or other material, all being techniques well known to the man skilled in the art. Impregnation under pressure is particularly advantageous when the substrate is wood or a wood composite material which is made to become wet during its life, for example, wood for window frames, timber used above ground in exposed environments such as decking and timber used in ground contact or fresh water or salt water environments.

The formulations of the invention are preferably used in immersion treatments of wood, in particular immersion treatments which utilise a vacuum and/or pressure. Thus, in a further aspect, the present invention provides a wood treatment system comprising a storage tank adapted to receive the wood to be treated and in said tank a volume of treatment solution comprising a biocidal agent and a stabilizer as defined herein. Optionally the system further comprises an autoclave. Optionally the system comprises means to apply a vacuum or pressure, e.g. 25-95% of a full vacuum and 8-12 Bar pressure.

Substrates made of wood or cellulosic material which have been treated with a formulation or product or by a method according to the invention as described herein, comprise further aspects of the present invention. Additionally, substrates made of wood or other cellulosic material containing a biocidal agent and a stabilizer (e.g. a formulation) according to the invention comprise a further aspect of the present invention.

A further aspect of the present invention is the use of formulations and products of the present invention in the treatment or preservation of wood or other cellulosic material.

In yet a further aspect, the invention provides a method of making a wood preservative formulation which comprises admixing a biocidal agent and a stabilizer as defined herein.

As described above, the stabilizer defined herein improve the penetration of biocidal agents into the treated wood; thus in a further aspect, the present invention provides the use of a stabilizer as defined herein to enhance the penetration into wood or other cellulosic material of biocidal agents which are co-administered to the wood or other material in a method of preservation. "Preservation" (and preserving) refers to the protection of wood or other material against fungal decay, borers and termites. Alternatively viewed, the present invention provides the use of a stabilizer as defined herein to ameliorate the impact on penetration into wood (or other cellulosic material) of biocidal agents which is caused by anionic by-products and timber extractives, as part of a method of preserving wood or other cellulosic material. Preferred methods of application and biocides are described above.

The invention will now be further described with reference to the following non-limiting Examples.

EXAMPLE 1

Materials and Methods

An aqueous solution of copper $2^+$ ions was prepared by reacting basic copper carbonate with mono ethanolamine (MEA) to give a copper concentration of 5% w/w and MEA concentration of 19.2% w/w, equivalent to an MEA:Copper molar ratio of 4:1.

3% w/v aqueous solutions of the copper amine complex were prepared with separate solutions dosed with 200 ppm of the cationic polymeric additives of the present invention. Additives 1 to 6 as incorporated are as follows:

| Additive No. | Chemical Group | CAS No. | Product Solution Strength, % | Viscosity, cps, 22° C. Sp 2, Sp 60 | Approximate Mw | pH | S.G., g/cm$^3$ | Freeze point, ° C. | Flash point, ° C. |
|---|---|---|---|---|---|---|---|---|---|
| 1 | Poly vinyl amine | 913068-94-7 | 24 | 10 | 1,000-4,000* | 4-6 | 1.12-1.14 | <0 | N/A |
| 2 | Low Mw Poly amine | 25988-97-0 | 50 | 12 | 2,000-4,000* | 4-7 | 1.12-1.16 | -3 | >100 |
| 3 | High Mw Poly amine | 25988-97-0 | 55 | 147 | 500,000-1,000,000* | 4-7 | 1.12-1.16 | -3 | >100 |
| 4 | poly DADMAC | 26062-79-3 | 40 | 45 | 30,000-50,000 | 3-4 | 1.1 | -3 | N/A |
| 5 | poly DADMAC Sulphone | 26470-16-6 | 40 | 6 | 4,000 | 3 | 1.14 | -5 | N/A |
| 6 | Poly allyl amine | 30551-89-4 | 20 | 15 | 3,000 | 12 | 1.03 | -5 | N/A |

*are estimates based on viscosity

Additive 1

Polyvinylamine, CAS 913068-94-7, 2-propen-1-aminium, N,N-dimethyl-N-2-propen-1-yl-, chloride (1:1), polymer with 2-propenamide, decarboxylated, hydrochlorides

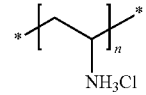

Additive 2

Polyamine, Poly(2-hydroxypropyldimethylammonium chloride) CAS 25988-97-0, low MW

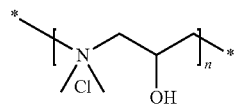

Additive 3
  Polyamine, Poly(2-hydroxypropyldimethylammonium chloride) CAS 25988-97-0, High MW

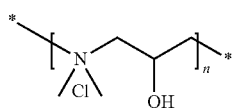

Additive 4
  PolyDADMAC (Diallyldimethylammoniumchloride), CAS 26062-79-3

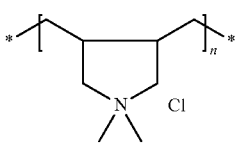

Additive 5
  PolyDADMAC-Sulphone, CAS 26470-16-6

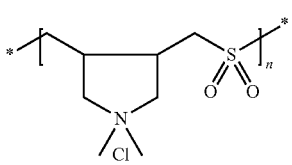

Additive 6
  Polyallylamine, CAS 30551-89-4

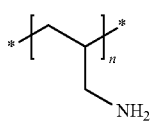

The 3% w/v aqueous solutions of the copper amine complex containing active substance were aged, to replicate commercial treatment plant solutions, by the addition of *Pinus Sylvestris* sapwood sawdust, 3.5% w/v, and stirred for 1 hour. The sawdust was filtered from of the aqueous the copper amine solution prior to treatment of matched blocks being undertaken.

Sections of kiln dried *Pinus Sylvestris* (12 cm×12 cm×2.75 cm) were then impregnated with a 3% w/v solution of the copper amine complex, using a double vacuum process.

Treatment Process:
  Weigh timber sample prior to treatment.
  Place timber sample in vacuum desiccator, apply vacuum to timber, 760 mm Hg, hold under vacuum for 20 minutes.
  Flood vessel under vacuum.
  Release vacuum, and soak at atmospheric pressure for 1 hour.
  Remove sample from solution, remove residual surface solution, then re-weigh timber sample.

Uptakes were determined and these expressed as a weight gain for the timber section. Retentions were also calculated as Kg/m3, (Weight of treatment solution per m3 of pine sapwood).

The depth of penetration was observed by cross cutting the samples and spraying with a reagent that reacts with copper to generate a dark coloration (dark blue to black).

Copper Spray Reagent:
  5% Sodium acetate solution
  0.5% Alcoholic Rubianic acid (Dithio-oxamide) solution
  Dissolve 5 g of sodium acetate in 100 ml of deionised water.
  Dissolve 0.5 g of Rubianic acid in 100 ml of ethanol or methanol.

The sodium acetate solution was sprayed onto a fresh cross cut face of timber and then the Rubianic acid solution was sprayed onto the fresh cross cut face of timber. The copper penetrated timber turns a dark blue to black colour instantly.

Results

| Chemical Group | Pre Treatment Wt, g | Post Treatment wt/g | Uptake/ g | Uptake Kg/m$^3$ | % Uptake vs no additive |
|---|---|---|---|---|---|
| No additive | 162.83 | 225.85 | 63.02 | 204.0 | 0 |
| Polyvinylamine | 161.09 | 348.05 | 186.96 | 605.3 | 197 |
| Polyamine | 156.37 | 286.96 | 130.59 | 422.8 | 107 |
| Polyamine | 161.83 | 246.19 | 84.36 | 273.1 | 34 |
| PolyDADMAC | 156.46 | 295.36 | 138.9 | 449.7 | 120 |
| PolyDADMAC-Sulphone | 158.29 | 282.61 | 124.32 | 402.5 | 97 |
| Polyallylamine | 158.62 | 243.70 | 85.08 | 275.4 | 35 |

For all products tested, gains in solution uptake (also reflected in the depth of penetration of the preservative in the timber) increased ~20-200% vs a solution with no additive. Results are also shown in FIG. 1.

EXAMPLE 2

The copper $^{2+}$ MEA solution, with 5% w/w copper concentration and an MEA:Copper molar ratio of 4:1 was prepared in accordance with the method in example 1.

Six 3% w/v aqueous solutions of the copper amine complex were prepared, with separate solutions dosed with 0, 10, 20, 30, 50 and 200 ppm of the cationic polymeric additive, additive no. 1 of the present invention, respectively.

The methods for aging the solution and treating matched blocks of *Pinus Sylvestris* was in accordance with those given in example 1.

Figure 2:
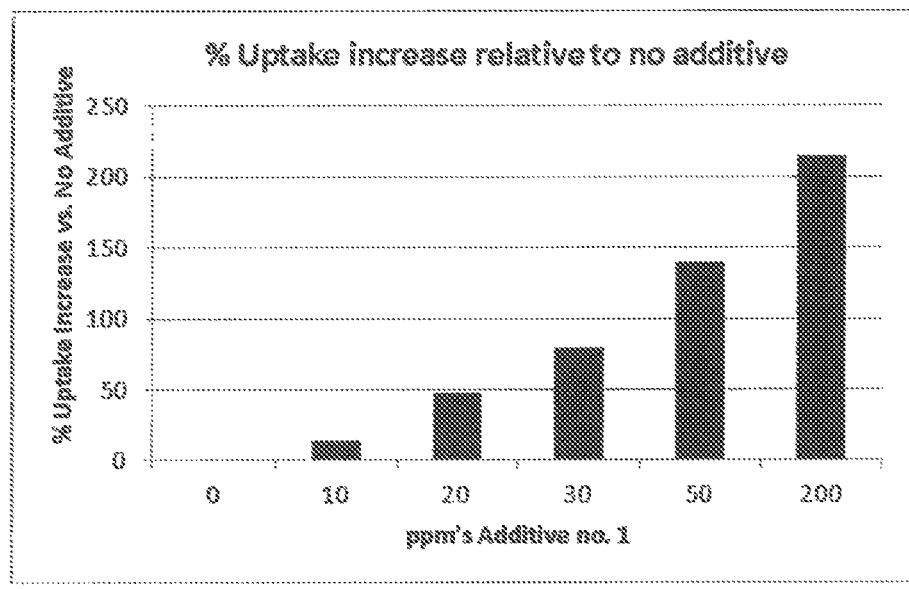
FIG. 2 is a graph showing % gains in solution uptake achieved during impregnation of a copper MEA solution into *Pinus sylvestris* with various concentrations of a cationic polymer additive of the invention.

Results are shown in FIG. 2.

EXAMPLE 3

An aqueous solution of zinc $^{2+}$ ions was prepared by reacting zinc chloride with sodium gluconate and mono ethanolamine to give a zinc concentration of 0.50% w/v and a Gluconate:Zn molar ratio of 2:1, and an MEA:Zn molar ratio of 2:1.

To separate aqueous solutions of the zinc gluconate/amine complex prepared was dosed 0 and 200 ppm of the cationic polymeric additive, additive no. 1 of the present invention, respectively.

The methods for aging the solution and treating matched blocks of *Pinus Sylvestris* was in accordance with those given in example 1.

Figure 3:
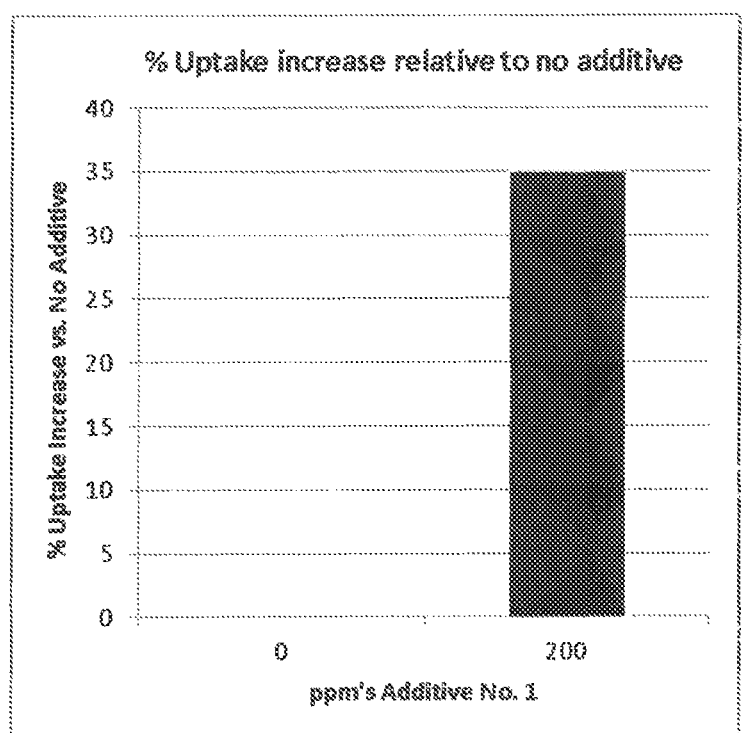
FIG. 3 is a graph showing % gain in solution uptake achieved during impregnation of a zinc/gluconate/MEA solution into *Pinus sylvestris* with a cationic polymer additive of the invention.

Results are shown in FIG. 3.

The invention claimed is:

1. A wood preservative formulation, comprising:
   a biocidal agent which comprises copper or zinc ion complexed with an amino compound selected from the group consisting of ammonia, a water-soluble amine or alkanolamine and an aminocarboxylic acid; and
   a stabilizer, said stabilizer selected from the group consisting of cationic polymers, enzymes, organic polymers, quaternary ammonium compounds, and mixtures thereof, wherein the quaternary ammonium compounds are selected from the group consisting of trimethyl alkyl quaternary ammonium compounds, dialkyldimethyl quaternary ammonium compounds and polyethoxylated quaternary ammonium compounds,
   wherein the wood preservative formulation further comprises organic fungicides selected from the group consisting of amides, anilides, anilinopyrimidine, aromatic compounds, fungicidal heterocyclic compounds, strobilurins, azoles, isothiazolones, cyclohexylhydroxydiazene 1-oxide, potassium salt, pyrion compounds, quaternary ammonium compounds and mixtures thereof,
   wherein the stabilizer is present in an amount effective to stabilize the wood preservative formulation thereby facilitating the wood preservative formulation to penetrate a wood substrate intended to be protected by the wood preservative formulation, and
   wherein the amount of the copper or zinc ion is greater than the amount of the stabilizer on a weight by weight basis.

2. The wood preservative formulation of claim 1, wherein the dialkyldimethyl quaternary ammonium compounds are selected from didecyl dimethyl ammonium chloride, didecyl dimethyl ammonium carbonate, didecyl dimethyl ammonium bicarbonate, dioctyl dimethyl ammonium chloride, octyl decyl dimethyl ammonium chloride, and mixtures thereof.

3. The wood preservative formulation of claim 1, wherein the stabilizer is a dialkyldimethyl quaternary ammonium compound.

4. The wood preservative formulation of claim 1, wherein the stabilizer is a didecyl dimethyl ammonium compound.

5. The wood preservative formulation of claim 1, wherein the stabilizer is didecyl dimethyl ammonium chloride, didecyl dimethyl ammonium carbonate, didecyl dimethyl ammonium bicarbonate, or mixtures thereof.

6. The wood preservative formulation of claim 1, wherein the formulation contains 0.01 to 4% by weight of the stabilizer.

7. The wood preservative formulation of claim 1, wherein the amino compound is monoethanolarnine or ammonia.

8. The wood preservative formulation of claim 1, further comprising an azole compound.

9. The wood preservative formulation of claim 1, wherein the stabilizer is selected from the group consisting of:
   poly vinyl formamides, poly amides, poly vinyl amides, polyamines,
   poly vinyl amines (PVAm),
   poly diallyldimethyl ammonium chlorides (D ADM AC's),
   poly allyl amines (PAAm),
   poly diallyldimethyl ammonium chlorides (DADMAC) Sulphones, and copolymers of vinyl amine and vinyl formamide.

10. The wood preservative formulation of claim 1 wherein the formulation is an aqueous solution.

11. A substrate of wood or other cellulosic material treated with the wood preservative formulations as defined in claim 1.

12. The wood preservative formulation of claim 1, wherein the ratio of copper or zinc ion to stabilizer is up to about 120:1.

13. The wood preservative formulation of claim 12, wherein the ratio of copper or zinc ion to stabilizer is up to about 30:1.

14. The wood preservative formulation of claim 13, wherein the ratio of copper or zinc ion to stabilizer is up to about 6:1.

15. A wood preservative formulation, comprising:
   a biocide agent which comprises a copper or zinc ion complexed with an amino compound selected from the group consisting of ammonia, a water-soluble amine or alkanolamine, and an aminocarboxylic acid; and
   a stabilizer, wherein the stabilizer is a quaternary ammonium compound selected from the group consisting of trimethyl alkyl quaternary ammonium compounds, dialkyldimethyl quaternary ammonium compounds, polyethoxylated quaternary ammonium compounds, and mixtures thereof,
   wherein the wood preservative formulation further comprises organic fungicides selected from the group consisting of amides, anilides, anilinopyrimidine, aromatic compounds, fungicidal heterocyclic compounds, strobilurins, azoles, isothiazolones, cyclohexylhydroxydiazene 1-oxide, potassium salt, pyrion compounds, quaternary ammonium compounds and mixtures thereof,
   wherein the stabilizer is present in an amount to inhibit the anti-penetrative effects of anionic by-products and timber extractives present in the preservative formulation thereby improving the ability of the wood preservative component to penetrate a wood substrate intended to be protected by the wood preservative formulation, and
   wherein the amount of the copper or zinc ion is greater than the amount of stabilizer on a weight by weight basis.

16. The wood preservative formulation of claim 15, wherein the stabilizer is a dialkyldimethyl quaternary ammonium compound.

17. The wood preservative formulation of claim 15, wherein the stabilizer is a didecyl dimethyl ammonium compound.

18. The wood preservative formulation of claim 15, wherein the formulation is an aqueous solution.

19. The wood preservative formulation of claim 15, wherein the ratio of copper or zinc ion to stabilizer is up to about 120:1.

20. The wood preservative formulation of claim 19, wherein the ratio of copper or zinc ion to stabilizer is up to about 30:1.

21. The wood preservative formulation of claim 20, wherein the ratio of copper or zinc ion to stabilizer is up to about 6:1.

22. A method of stabilizing a wood treatment formulation that contains a copper or zinc ion complexed with an amino compound selected from the group consisting of ammonia, a water-soluble amine or alkanolamine, and an aminocarboxylic acid, comprising:
   adding a stabilizer to the wood treatment formulation to prepare the wood preservative formulation of claim 1, wherein the stabilizer is present in an amount to inhibit the anti-penetrative effects of anionic by-products and timber extractives present in the preservative formulation thereby improving the ability of the wood preservative formulation to penetrate a wood substrate intended to be protected by the wood preservative formulation, and wherein the amount of copper or zinc ion is greater than the amount of the stabilizer added on a weight by weight basis.

23. The method of claim 22, wherein the wood treatment formulation further comprises an azole.

24. The method of claim 22, wherein the stabilizer is a didecyl dimethyl ammonium compound.

25. The method of claim 22, wherein the ratio of copper or zinc ion to stabilizer is up to about 120:1.

26. The method of claim 25, wherein the ratio of copper or zinc ion to stabilizer is up to about 30:1.

27. The method of claim 26, wherein the ratio of copper or zinc ion to stabilizer is up to about 6:1.

* * * * *